United States Patent [19]
Greco et al.

[11] Patent Number: 6,030,768
[45] Date of Patent: Feb. 29, 2000

[54] ANALYSIS OF CONFORMATIONAL CHANGES IN BAND 3 PROTEIN AS A METHOD FOR DIAGNOSING ALZHEIMER'S DISEASE

[75] Inventors: Frank A. Greco, Lexington; A. K. Solomon, Cambridge, both of Mass.

[73] Assignee: President and Fellows of Harvard College, Cambridge, Mass.

[21] Appl. No.: 08/931,216

[22] Filed: Sep. 16, 1997

[51] Int. Cl.$^7$ .............................. C12Q 1/00; C12N 5/00; C12N 5/08; G01N 33/53

[52] U.S. Cl. .............................. 435/4; 435/325; 435/366; 435/968; 424/93.73; 424/529; 424/533

[58] Field of Search ................................ 424/93.73, 529, 424/533; 435/325, 4, 366, 968

[56] References Cited

PUBLICATIONS

Stryer, L. Biochemistry, third edition, p. 25, 1988.
Bohinski, R.C. Modern Concepts in Biochemistry, fifth edition, pp. 148–149 and 164–168, 1987.
Morris, JC et al, Neurology 39: 1159–1165, 1989.
McKhann, G et al, Neurology 34: 939–944, 1984.
Bruce, LJ et al, Biochem. Journal 293: 317–320, 1993.
Salhany, JM et al, Biochem. Journal 317: 509–514, 1996.
Pratt, WB et al, Principles of Drug Action, third edition, pp. 2 and 71, 1990.
Erythrocyte Membrane Characteristics Indicate Abnormal Cellular Aging in Patients with Alzheimer's Disease, Bosman et al., 1991, Neurobiology of Aging, vol. 12, pp. 13–18.
Erythrocyte Aging Characteristics in Elderly Individuals with Beginning Dementia, Bosman et al., 1997, Neurobiology of Aging, vol. 18, No. 3, pp. 291–295.
Kinetics of Chloride–Bicarbonate Exchange Across the Human Red Blood Cell Membrane, Greco et al., 1997, J. Membrane Biol., vol. 159, pp. 197–208.
Evaluation of Dementia, Geldmacher et al., 1996, New England Journal of Medicine, vol. 335, No. 5, pp. 330–336.
Assembly of Microtubule–Associated Protein Tau into Alzheimer–like Filaments Induced by Sulphate Glycosaminoglycans, Geodert et al., 1996, Nature, vol. 383, pp. 550–553.
Disruption of the Cytoskeleton in Alzheimer's Disease, Lee, Current Opinion in Neurobiology, 1995, vol. 5, pp. 663–668.
The Molecular Pathology of Alzheimer's Disease, Selkoe, 1991, Neuron, vol. 6, pp. 487–498.
A Molecular Approach to Alzheimer's Disease, Multhaup et al., 1993, Biol. Chem. Hoppe–Seyler, vol. 374, pp. 1–8.
Processing of Alzheimer A–Beta–Amyloid Precursor Protein: Cell Biology, Regulation, and Role in Alzheimer Disease, Gandy et al., 1994, International Review of Neurobiol., vol. 36, pp. 29–50.
Apolipoprotein E Alleles as Risk Factors in Alzheimer's Disease, Roses, 1996, Annu. Rev. Med., vol. 47, pp. 387–400.
Extraneuronal Manifestations of Alzheimer's Disease, Scott, 1993, JAGS, vol. 41, pp. 268–276.
Amyloid Beta–Protein Disposition in Tissues Other Than Brain in Alzheimer's Disease, Joachim et al., 1989, Nature, vol. 341, pp. 226–230.
Preparation of Impermeable Ghosts and Inside–out Vesicles from Human Erythrocyte Membranes, Steck et al., 1974, J. Cell. Biol., vol. 62, pp. 172–180.

*Primary Examiner*—Anthony C. Caputa
*Assistant Examiner*—John K. Weatherspoon
*Attorney, Agent, or Firm*—Wolf, Greenfield & Sacks, P.C.

[57] ABSTRACT

A method diagnosing Alzheimer's disease in a patient includes analyzing conformational changes in a band 3 protein of the patient yielding a time course of the conformational changes. One approach includes analyzing conformational changes in a band 3 protein by measuring band 3 $Cl^-/HCO_3^-$ exchange over time. In this approach a double exponential function is solved for two rate constant estimates by fitting the double exponential function to the time course. At least one of the rate constant estimates is used to determine whether the patient has Alzheimer's disease. A second approach includes analyzing conformational changes in a band 3 protein by measuring the emission spectrum of a stilbene bound to band 3, which emission changes in response to band 3 conformational changes. In this approach, a single exponential function is solved for a parameter by fitting the single exponential function to the time course obtained. The parameter estimate is used to determine whether the patient has Alzheimer's disease.

10 Claims, 6 Drawing Sheets

ANALYSIS OF CONFORMATIONAL CHANGES IN BAND 3 PROTEIN AS A METHOD FOR DIAGNOSING ALZHEIMER'S DISEASE

FIELD OF THE INVENTION

The present invention relates to methods for diagnosing Alzheimer's disease in a patient based on non-central nervous system manifestations of Alzheimer's disease.

BACKGROUND OF THE INVENTION

Alzheimer's disease (AD) is a neurodegenerative disease for which there is at present no cure. AD causes dementia in about 10% of the population above the age of 65 (Geldmacher and Whitehouse, *N. Eng. J. Med.* 335:330, 1996). Due to the widespread nature of the disease in the population of aging persons, much research has been conducted to determine the underlying cause or causes of AD so that treatments can be developed. There are several theories as to the processes underlying AD, including abnormal protein tau (Goedert et al., *Nature* 383:550 (1996); Lee, *Curr. Opin. Neurobiol.* 5:663 (1995)), aberrant processing of the β-amyloid precursor protein (Selkoe, *Neuron* 6:487 (1991); Multhaup et al., *Biol. Chem. Hoppe-Seyler* 374:1 (1993); Gandy and Greengard, *Int. Rev. Neurobiol.* 36:29 (1994)) and expression of apolipoprotein E (Roses, *Annu. Rev. Med.* 47:387 (1996)). Even with the significant amount of research into AD, no cause has yet been identified. Consequently, no definitively efficacious treatments have been developed for alleviating the effects of the neurodegeneration of AD. Nevertheless, several studies have demonstrated that persons treated with compounds such as nonsteroidal antiinflammatory drugs NSAIDs), estrogen, vitamin E, or nicotine have lower rates of AD than the general population The only certain diagnosis of AD to date is via postmortem analysis of an individual's brain. The brain tissue of persons afflicted with AD exhibits a characteristic accumulation of neurofibrillary tangles which include the processed β-amyloid protein. While post-mortem diagnosis is unequivocal, it clearly does not inform a patient's physician within a time that the physician could attempt therapeutic measures.

While it is thought that the pathophysiology of AD arises in the central nervous system (CNS), there are non-CNS manifestations of AD, including changes in the blood and the skin (Scott, *J. Am. Geriatr. Soc.* 41:268 (1993); Joachim et al., *Nature* 341:226 (1989)). Advantageously, these non-CNS manifestations of AD involve physiological processes which can be tested in tissues accessible by non-invasive or minimally invasive procedures. Some progress has been made toward the diagnosis of AD in living patients by measuring the differences between physiological processes of normal individuals and those of AD patients. Unfortunately, diagnostic procedures based on such differences are presently not reliable predictors of progression to AD.

One example of such a non-CNS physiological process which may be useful for diagnosing AD is the transport of anions by the erythrocyte (red blood cell) membrane transporter band 3. Bosman et al. (*Neurobiol Aging* 12:13–18, 1991) postulated that AD might be the result of accelerated cellular aging of the neurons affected in AD. These investigators examined the parameters which were known to reflect the aging of the erythrocyte, including increased quantities of erythrocyte-bound immunoglobulin G (IgG) and altered anion transport by band 3. The latter parameter was determined by sulfate ion transport and analyzed using standard Michaelis-Menten kinetics.

The foregoing methods of analysis are inadequate for reliable diagnosis of AD in living persons. Thus, there is a need for methods of diagnosis of AD which are reliable, accurate, sensitive, non-invasive or minimally invasive, and which can be performed quickly and inexpensively using existing laboratory equipment. Further, there is a need for methods which can track the progression of AD. Accurate diagnostic methods will be of use in providing patients and physicians with information needed for responding to the personal and medical effects of AD.

SUMMARY OF THE INVENTION

It has now been discovered that these limitations can be overcome by diagnostic methods which more accurately measure changes in the conformation of erythrocyte band 3. In certain embodiments, such methods include improved analysis of anion transport as a measure of band 3 conformation changes. In other embodiments, such methods include direct measurement of conformation changes to band 3 by alterations in the emission spectra of molecules which bind to band 3, such as stilbenes.

One embodiment of the invention is directed to a method of diagnosing AD in a patient including the following steps: analyzing conformational changes in a band 3 protein of the patient yielding a time course of the conformational changes; dividing the time course into first and second time periods; solving first and second single exponential functions for estimates of rate constant parameters by respectively fitting the first and second single exponential functions to the first and second time periods; and determining whether the patient has AD using at least one of the two rate constant parameter estimates.

In an embodiment, the method further includes, after the step of solving first and second single exponential functions, a step of solving a double exponential function for better estimates of the two rate constant parameters.

In an embodiment, the step of analyzing includes obtaining a time course of fluorescence representing the conformational changes in the band 3 protein.

In an embodiment, the step of analyzing further includes converting the time course of fluorescence to a time course of chloride changes.

Another embodiment of the invention is directed to a method of diagnosing AD in a patient comprising the following steps: analyzing conformational changes in a band 3 protein of the patient using a fluorescent probe of band 3 protein conformation which binds to band 3 yielding a time course of the conformational changes; solving a single exponential function for an estimate of a rate constant parameter in the single exponential function by fitting the single exponential function to the time course; and determining whether the patient has AD using the parameter estimate.

The features and advantages of the present invention will be more readily understood and apparent from the following detailed description of the invention, which should be read in conjunction with the accompanying drawings and from the claims which are appended to the end of the detailed description.

BRIEF DESCRIPTION OF THE DRAWING

For a better understanding of the present invention, reference is made to the accompanying drawings, which are incorporated herein by reference and in which.

DETAILED DESCRIPTION

Figure 1A:
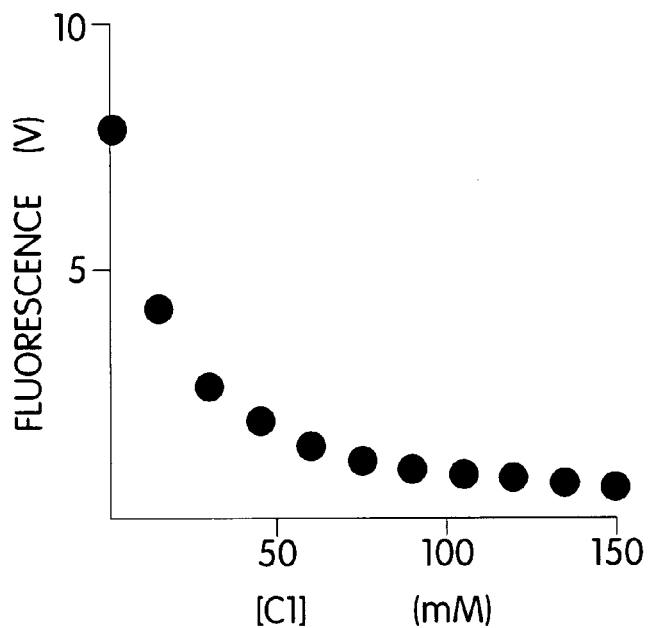
FIG. 1A is a graph showing the fluorescence of a solution of SPQ as a function of NaCl.

The invention provides improved methods of diagnosis of AD, based on the measurement and analysis of conformational changes of erythrocyte band 3 protein. The conformational changes are measured with the aid of direct or indirect molecular probes of band 3 conformation. A direct molecular probe is a molecule which binds to band 3 and has one or more properties which change in relation to the physical conformational changes of band 3. An indirect molecular probe is a molecule which does not necessarily bind to band 3, but has one or more properties which change in relation to the effects of the conformational changes of band 3. Indirect molecular probes include molecules which measure a change in activity of band 3, such as anion transport.

By the methods of the invention, a time course of conformational changes of band 3 is obtained. In one embodiment of the invention, a single exponential function is fit to the time course. A parameter (variable) of the single exponential function is determined and is used to classify the patient as having, or not having, AD. In another embodiment, a double exponential function is fit to the time course. Parameters of the double exponential function are obtained and are used to classify the patient.

According to one aspect of the invention, methods for diagnosing AD are provided, which involve measuring conformational changes in band 3 by measuring the anion exchange activity of band 3 in erythrocytes, preferably in hemoglobin-free erythrocyte ghosts prepared by standard methods ("hemoglobin-free erythrocyte ghosts" are erythrocyte ghosts from which the hemoglobin has been substantially removed). The anion exchange measured preferably is Cl$^-$/HCO$_3^-$ exchange, although, as will be apparent to one of ordinary skill in the art, other anions transported by band 3 (e.g. sulfate) can alternatively be measured. Preferably Cl$^-$/HCO$_3^-$ exchange is measured by preparing erythrocyte ghosts containing chloride ions and a fluorescent probe of chloride ion concentration, contacting the ghosts with HCO$_3^-$ to initiate Cl$^-$/HCO$_3^-$ exchange by band 3 and measuring the change in fluorescence of the probe over time to determine the rate of Cl$^-$/HCO$_3^-$ exchange by band 3. In a preferred embodiment, exemplified below, the fluorescent molecular probe 6-methoxy-N-(3-sulfopropyl)quinolinium (SPQ) is used. Other molecules which can act as indirect molecular probes of anions transported by band 3 are standard in the art and can be tested for use in the methods disclosed herein. Preferably, as will be described in greater detail below, in this embodiment, a double exponential function is fit to the time course of [Cl$^-$exchange. Two rate constant parameters of the double exponential function are obtained and are used to classify a patient.

According to another aspect of the invention, methods for diagnosing AD by directly analyzing the conformational change of erythrocyte band 3 protein are provided. By "directly" analyzing it is meant determining a characteristic of a direct molecular probe which binds band 3 and which characteristic changes in accordance with conformational changes of band 3. For example, the class of molecules known as stilbenes are known as inhibitors of band 3 function which bind directly to the band 3 protein. The stilbenes are fluorescent molecules, and it has been discovered that the emission spectrum of stilbene bound to band 3 changes in response to band 3 conformational changes. Thus, the stilbenes are fluorescent probes of band 3 protein conformation. Measurement of the changes in emission spectra provides a predictor of the conformational changes of band 3 which are characteristic of persons having AD. Preferably, in this embodiment, a single exponential function is fit to the time course of fluorescence. A parameter of the single exponential function is obtained and is used to classify the patient. Alternatively, a double exponential function may be fit to the time course, and at least one parameter of the double exponential function used to classify the patient.

Preferably, the stilbene used is 4,4'-dibenzoamido 2,2'-disulfonic stilbene (DBDS), although one of ordinary skill in the art can readily test other stilbenes according to the methods disclosed herein to determine the suitability of a particular stilbene for use in methods of diagnosing AD. Other stilbenes include, for example, N,N,N',N'-tetrabenzyl4,4'-diaminostilbene-2,2'-disulfonate (TBenzDS), 4,4'-diacetamido-2,2'-stilbene disulfonate (DAS), 4,4-dinitrostilbene-2,2'-disulfonate (DNDS), 4,4'-diisothiocyanodihydrostilbene-2,2'-disulphonate (H$_2$DIDS), 4,4'-diisothiocyanostilbene-2,2'-disulphonate (DIDS), 4-acetamido-4'-isothiocyanostilbene-2,2'disulphonate (SITS), 4-benzamido4'-aminostilbene-2-2'disulphonic acid (BADS) and 4,4'-diaminostilbene-2,2'-disulphonate (DADS). Other molecules which bind band 3 and have characteristics alterable by conformational changes of band 3 likewise can be used in the methods disclosed herein.

With respect to measuring a conformational change of band 3 protein by a molecular probe as described above, the measurement preferably is of an easily detectable characteristic of the molecular probe. In the examples provided herein, the preferred molecular probes (e.g. SPQ, DBDS) are fluorescent probes. Thus, measurement of the conformational change can be made by measuring fluorescence using standard methods such as the use of a spectrometer. Other parameters which easily are measurable include luminescence, enzymatic activity, and the like. It is within the skill of the artisan to determine which easily measurable parameter of a molecular probe can be used in the methods disclosed herein.

According to a preferred embodiment of the invention, measurement of the anion transport activity of band 3 was conducted as follows. 6-methoxy-N-(3-sulfopropyl) quinolinium (SPQ, Molecular Probes, Eugene, Oreg.) was prepared as a 20 mM stock solution in 5 mM $Na_2HPO_4$, pH 8, and stored frozen in aliquots. $NaHCO_3$ solutions were freshly prepared before each measurement in 10 mM $Na_2HPO_4$. Each solution was adjusted to pH 7.4 and kept in a syringe anaerobically until use.

The hemoglobin-free red blood cell ghosts ("white" ghosts) were loaded and resealed to contain 10 mM SPQ, 10 mM $Na_2HPO_4$, pH 7.4, and either 150 mM NaCl or $NaHCO_3$ in the following manner. Ghosts were prepared by a modification of the method of Steck and Kant (*Methods Enzymol.* 31:172–180, 1974). Citrate-anticoagulated human blood was used within 24 h of collection. Following three washes in normal saline, the cells were hemolysed in 5 mM $Na_2HPO_4$, pH 8, on ice. Ghosts were washed in lysing medium three times by centrifugation at 10,000 g for 10 min at 4° C. 1 ml of pellet was added to 1 ml of 20 mM SPQ stock solution and incubated on ice for 5 min. Salt was added to bring the concentration to 150 mM NaCl or $NaHCO_3$. Following a second 5 min incubation on ice, the ghosts were resealed by incubation at 37° C. for 1 h. Resealed ghosts were washed three times and the resulting pellet was resuspended 1:50 (vol/vol) in 10 mM $Na_2HPO_4$, pH 7.4, and either 150 mM NaCl or $NaHCO_3$.

Fluorescence measurements were performed on a Model SF.17MV Stopped-flow Spectrometer (Applied Photophysics, Leatherhead, UK). SPQ excitation was at 350 nm (9 nm bandpass) with emission measured through a 3 mm Corion cut-on filter with 50% transmission at 500 nm. Compressed air at 40 psi injected equal volumes of ghosts and mixtures into a mixing chamber; a stop syringe (0.1 ml) triggered recording. For all measurements, $[HCO_3^-]=0.15$ M-$[Cl^-]$. A circulating waterbath (Model 1145, VWR, Westchester, Pa.) maintained the drive syringes and mixing chamber at 4±0.1° C. Four hundred data points were collected over 10 s and stored in the spectrometer's workstation. Seven to ten replicate measurements were made at each $[Cl^-]$. A small decrease in fluorescence occurs when ghosts are mixed with their suspending buffer. This baseline was subtracted from each measurement prior to converting fluorescence to $[Cl^-]$. A mixing artifact, usually less than 25 msec, was truncated from the data before conversion.

With the above-described method, the amount of fluorescence of band 3 is analyzed over time yielding a time-line of fluorescence in band 3. In one embodiment of the invention, as will be described in greater detail below, this time-line of fluorescence is converted to a time-line of internal chloride [Cl–] concentration. The time-line of chloride $[Cl^-]$ concentration, in one embodiment, then is divided into two time periods. A first single exponential function is fitted to one of the two time periods. A first initial amplitude estimate and a first initial rate constant estimate, both parameters of the first single exponential function, are determined. A second single exponential function is fitted to the other time period. A second initial amplitude estimate and second initial rate constant estimate, both parameters of the second single exponential function, are determined. The initial estimates may be determined using a least mean squares (LMS) approach.

As will be described, the two initial rate constant estimates may be used to determine whether or not the patient has AD.

To obtain better estimates of the rate constants, used to classify the patient, a double exponential function is fitted to the entire time course of internal chloride $[Cl^-]$ concentration. In solving for better estimates of the two rate constants, the initial amplitude estimates and initial rate constant estimates are used. An LMS approach may be used to determine the better rate constant estimates. At least one of the better estimates of the rate constants may be used to classify the patient.

The steps listed above relating to conversion, equation solving and patient classification will now be described in greater detail.

Conversion of Fluorescence to Internal Chloride

For solutions of NaCl, the fluorescence of SPQ follows the following Stern-Volmer equation:

$$\frac{F_0}{F} = 1 + K[Cl^-]$$

where $F_0$ is the fluorescence at $[Cl^-]=0$ and K is the quench constant. For ghosts loaded with 150 mM $NaHCO_3$, the Stern-Volmer equation is used to convert the time course of fluorescence to that of internal chloride.

For ghosts loaded with 150 mM NaCl, the relationship between fluorescence and chloride concentration approximates a straight line. Thus, a linear conversion factor is used to convert the time course of fluorescence to that of chloride.

FIGS. 1A and B illustrate the fluorescence of SPQ versus chloride in an aqueous solution. FIG. 1A shows the fluorescence of a solution of SPQ as a function of NaCl, as indicated by $[Cl^-]$, wherein fluorescence in volts as measured by a photomultiplier tube is shown along the vertical axis and NaCl in mM is shown along the horizontal axis.

Figure 1B:
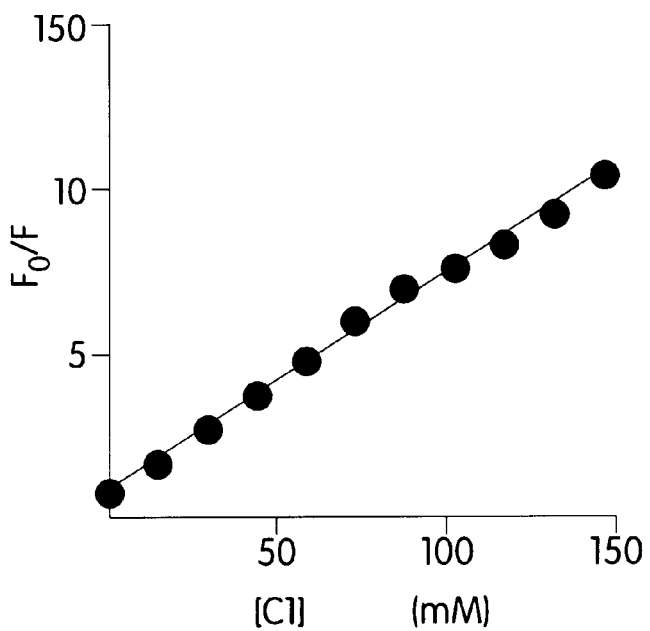
FIG. 1B is a graph showing the Stern-Volmer plot of the fluorescence plot shown in FIG. 1A.

FIG. 1B shows the Stern-Volmer plot of the fluorescence plot shown in FIG. 1A. As can be seen, the relationship between fluorescence and chloride concentration approximates a straight line.

Figure 2A:
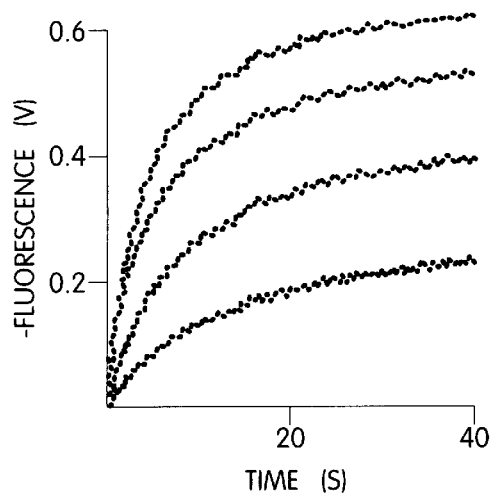
FIG. 2A is a graph showing the time course of fluorescence of a solution of ghosts loaded with 150 mM NaHCO$_3$ in a graded series of Cl$^-$/HCO$_3^-$ mixtures.

FIGS. 2A–D illustrate data obtained in converting the time course of fluorescence to chloride $[Cl^-]$ concentration. FIG. 2A is a graph showing the time course of fluorescence of a solution of ghosts loaded with 150 mM $NaHCO_3$ and a graded series of $Cl^-/HCO_3^-$ mixtures. The curves have been translated to align the origins with one another and inverted. Fluorescence in volts as measured by a photomultiplier tube is shown along the vertical axis and time in seconds is shown along the horizontal axis. The four curves shown correspond respectively, in order of increasing fluorescence amplitude, to mixtures having initial gradients of 15, 30, 45 and 60 mM, in this instance, inward of $Cl^-$, outward for $HCO_3^-$.

Figure 2B:
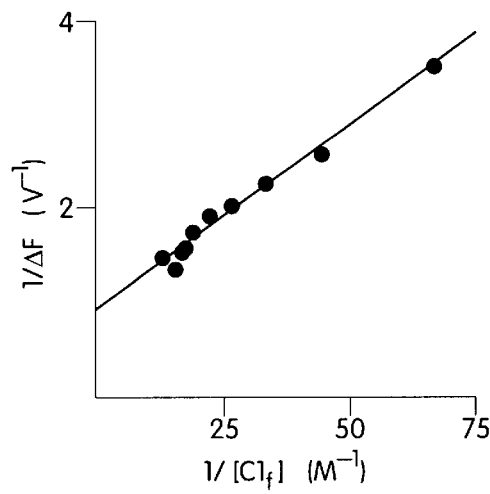
FIG. 2B is a plot of $$\frac{1}{F_i - F_f} \text{ versus } \frac{1}{[Cl_f^-]};$$

FIG. 2B is a plot of $$\frac{1}{F_i - F_f} \text{ versus } \frac{1}{[Cl_f^-]},$$

where $F_i$ and $F_f$ respectively are the initial and final measured fluorescence values, illustrating a method of obtaining the Stern-Volmer parameters.

Figure 2C:
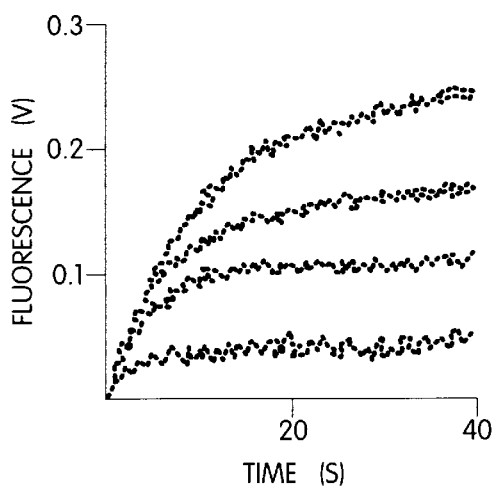
FIG. 2C is a graph showing the time course of fluorescence of a solution consisting of ghosts loaded with 150 mM NaCl in a graded series of Cl$^-$/HCO$_3^-$ mixtures.

FIG. 2C is a graph showing the time course of fluorescence of a solution consisting of ghosts loaded with 150 mM NaCl and a graded series of $Cl^-/HCO_3^-$ mixtures. Like FIG. 2A, the curves have been translated to align the origins. The four curves respectively correspond, in order of increasing fluorescence amplitude, to initial gradients of 15, 30, 45 and 60 mM, in this instance, outward for $Cl^-$ and inward for $HCO_3^-$.

Figure 2D:
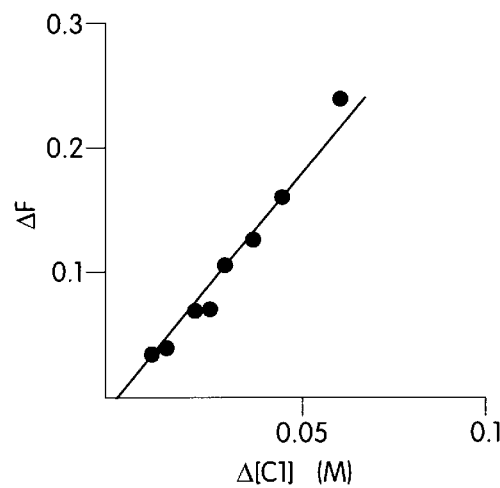
FIG. 2D is a plot of $\Delta F$ versus $\Delta[Cl^-]$.

FIG. 2D is a plot of ΔF versus Δ[Cl⁻]. For each point in the time course, 0.15−Cl⁻ was calculated by dividing F(t)−F(0) by the slope of the plot.

Curve Fitting

After converting the time course of fluorescence to that of internal chloride [Cl⁻], a double exponential function is fit to the entire time course. An example of a suitable double exponential function is the following:

$$C(t) = a1\, e^{(-k1t)} + a2\, e^{(-k2t)} + Ceq.,$$

where a1 and a2 respectively are first and second amplitudes and k1 and k2 respectively are first and second rate constants, as used herein. The double exponential function may be fit to the entire time course by the LMS method.

The LMS method requires initial estimates of the amplitudes a1 and a2 and rate constants k1 and k2, and the value of Ceq. is given by the [Cl⁻] level in the solution mixed with the ghosts.

Initial estimates of the amplitudes and rate constants may be obtained by first dividing the time course into two periods. Such periods, for example, may include less than one second, and greater than and equal to one second. Then, a single exponential function is fit to the first time period, between zero and one second in this example. The following equation is an example of a single exponential function that may be used:

$$C(t) = b1\, e^{(-l1t)} + d1.$$

Then, the parameters b1, l1 and d1 are determined, using an LMS method, for example.

Similarly, a single exponential function is fit to the second time period, between one and ten seconds in this example. The following single exponential function is an example of one that may be used:

$$C(t) = b2\, e^{(-l2t)} + d2.$$

Then, the parameters b2, l2 and d2 are determined, using an LMS method, for example.

The values obtained for amplitudes b1 and b2 respectively are used as the initial estimates of amplitudes a1 and a2 in the double exponential function. Similarly, the values for l1 and l2 respectively are used as the initial estimates for the rate constants of k1 and k2 in the double exponential function. Then, the double exponential function may be fit to the entire time course of chloride [Cl⁻], such as by the LMS method. In this manner, better estimates of rate constants k1 and k2 are obtained for each [HCO₃⁻].

As described below, the estimates for the rate constants k1 and k2 may be used to classify a subject as having, or not having, AD. As an alternative to solving the double exponential function, the initial estimates for the rate constants, those being l1 and l2, obtained by fitting each of two single exponential functions to different time periods of the time course, may be used to classify the subject. The better estimates of the rate constants k1 and k2, obtained by solving the double exponential function, however, may yield more accurate classification.

Figure 3A:
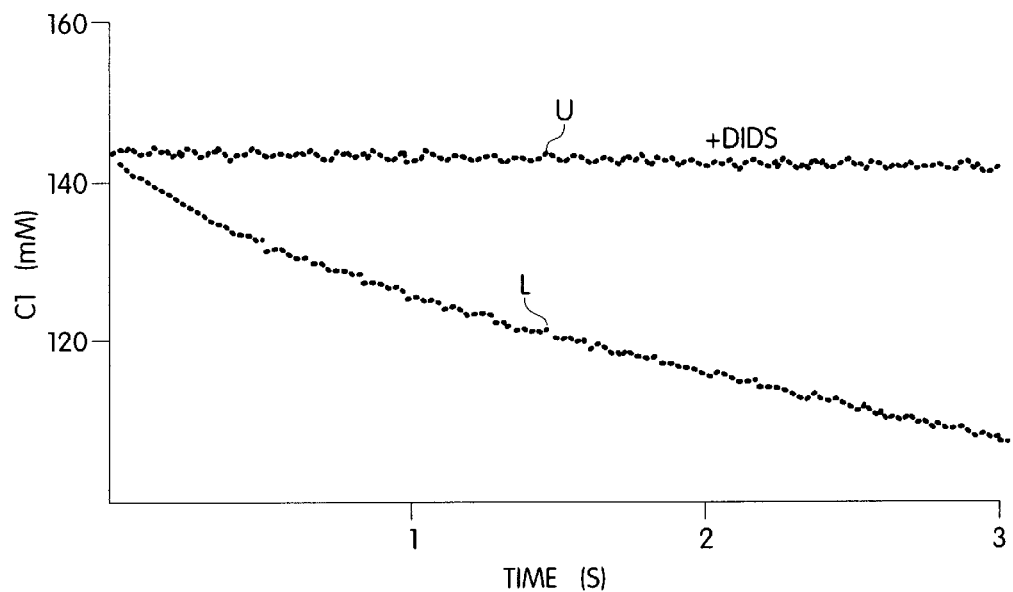
FIG. 3A is a graph of the initial time course of the level of internal chloride [Cl$^-$] in ghosts loaded with 0.15 M NaCl in response to a 0.075 M gradient.

FIG. 3A is a graph of the initial time course of the level of internal chloride [Cl⁻] in ghosts loaded with 0.15 M NaCl in response to a 0.075 M gradient. This time course is shown as the lower of the two curves (labelled L) in FIG. 3A. Shown on the horizontal axis is time in seconds and shown along the vertical axis is the level of [Cl⁻] in mM.

Incubation at 37° C. in 300 μM Na₂DIDS for one hour during the resealing step completely abolishes anion exchange as shown in the upper curve (labelled U) in FIG. 3A.

Figure 3B:
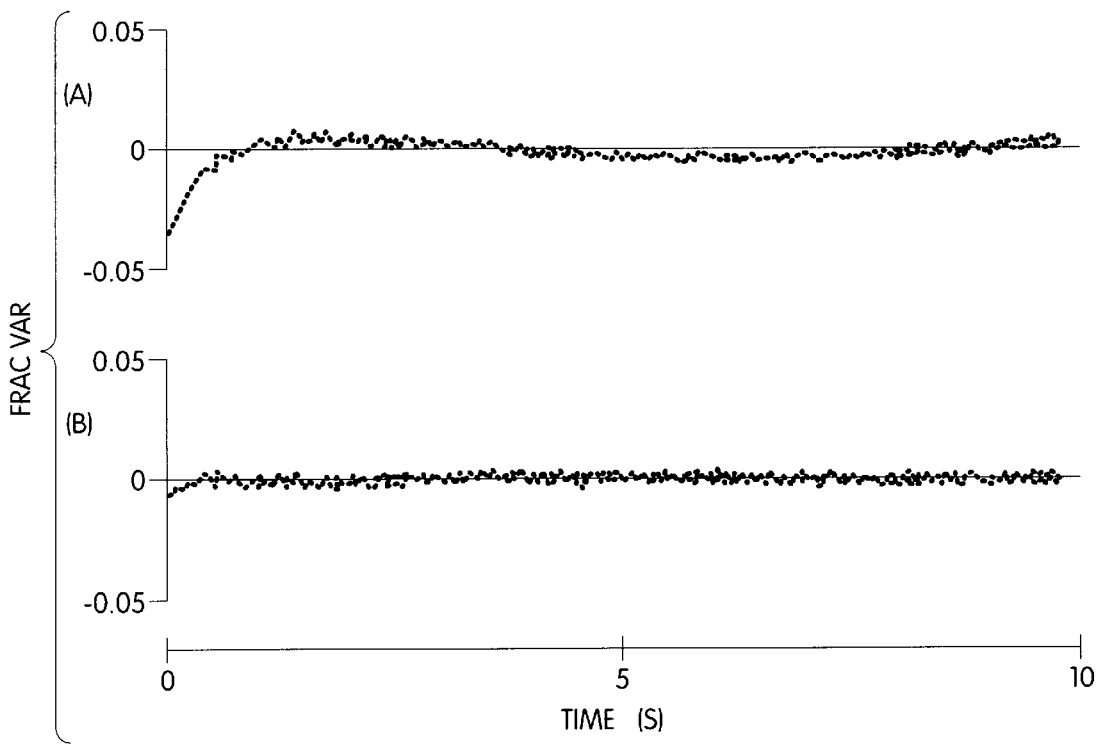
FIG. 3B is a graph showing two time curves along the same time axis illustrating respective fractional variances of fitting a single exponential function to a time course of chloride and fitting a double exponential function to the same time course of chloride.

FIG. 3B includes two time curves along the same time axis (horizontal) illustrating respective fractional variances of (1) the fitting of a single exponential function to the time course of chloride (upper curve), and (2) the fitting of a double exponential function to the same time course of chloride (lower curve). As can be seen in the upper curve, labelled (A), the greatest deviation in the single exponential function fit occurs during about the first three seconds in time. By comparing the upper curve to the lower curve, labelled (B), one can see the remarkable improvement in variance in the double exponential function fit to the same time course.

Classification of Subjects

The rate constant parameter k1 does not vary in theory with the level of [HCO₃] but has some variation due to experimental error. The value assigned to rate constant k1 to classify a subject is the average of the values of k1 obtained at each [HCO₃⁻] level.

The rate constant parameter k2 does depend upon the level [HCO₃]. In one embodiment of the invention, the value selected for rate constant k2 to classify a subject is that obtained at [HCO₃]=2.5 mM and is labelled k2 (22.5).

In an embodiment of the invention, the number 0.16 k1+3.7k2(22.5) is calculated. If that number exceeds 1.0, then the subject is classified as having AD. If that number does not exceed 1.0, then the subject is classified as not having AD.

Figure 4A:
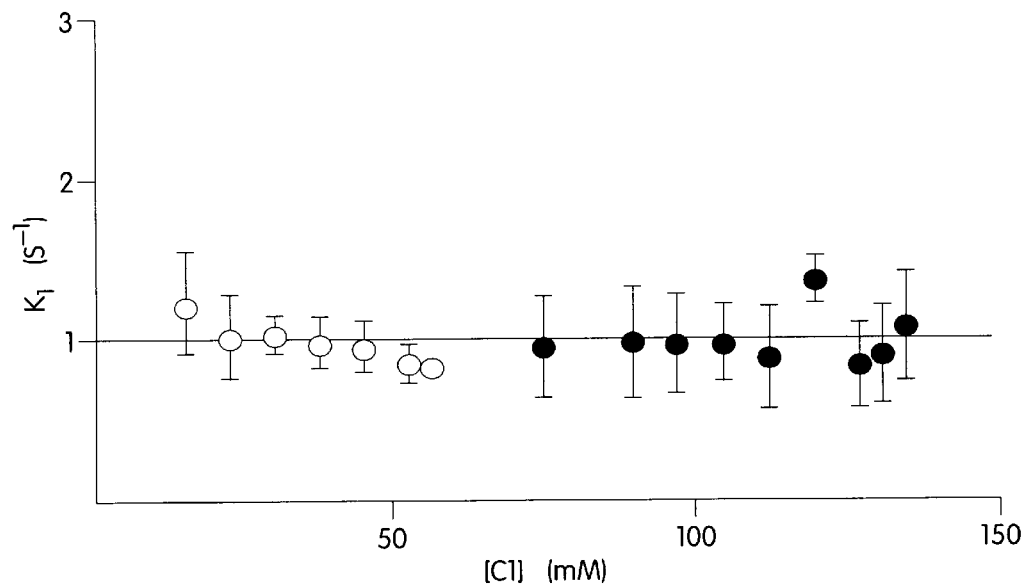
FIGS. 4A and 4B are graphs illustrating the dependence of rate constant parameters upon medium composition.

FIGS. 4A and B are graphs illustrating the dependence of rate constant parameters k1 and k2 upon medium composition. The symbols in the graphs are as follows: ○=data obtained from ghosts loaded with 150 mM NaHCO₃, with inward Cl⁻ gradients and outward HCO₃⁻ gradients; ●=represent data obtained from ghosts loaded with 150 mM NaCl, with outward Cl⁻ and inward HCO₃⁻ gradients.

FIG. 4A is a graph of right constant k1 (along the vertical axis) versus Cl⁻ (along the horizontal axis). K1 does not depend upon medium composition.

$K_1$ is equal to 1.04±0.014 S⁻.

Figure 4B:
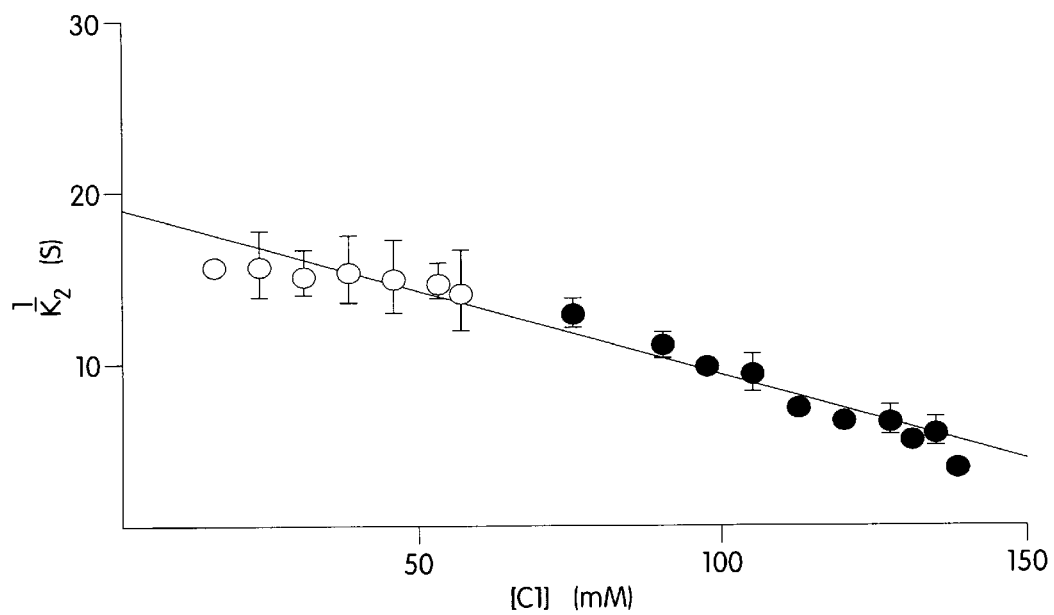

FIG. 4B is a plot of $$\frac{1}{K2}$$

(along the vertical axis) versus [Cl⁻] in mM (along the horizontal axis). The plot approximates a straight line.

$$\frac{1}{K2}$$

is equal to 18.8S−0.095 mM⁻S [Cl⁻].

Figure 5A:
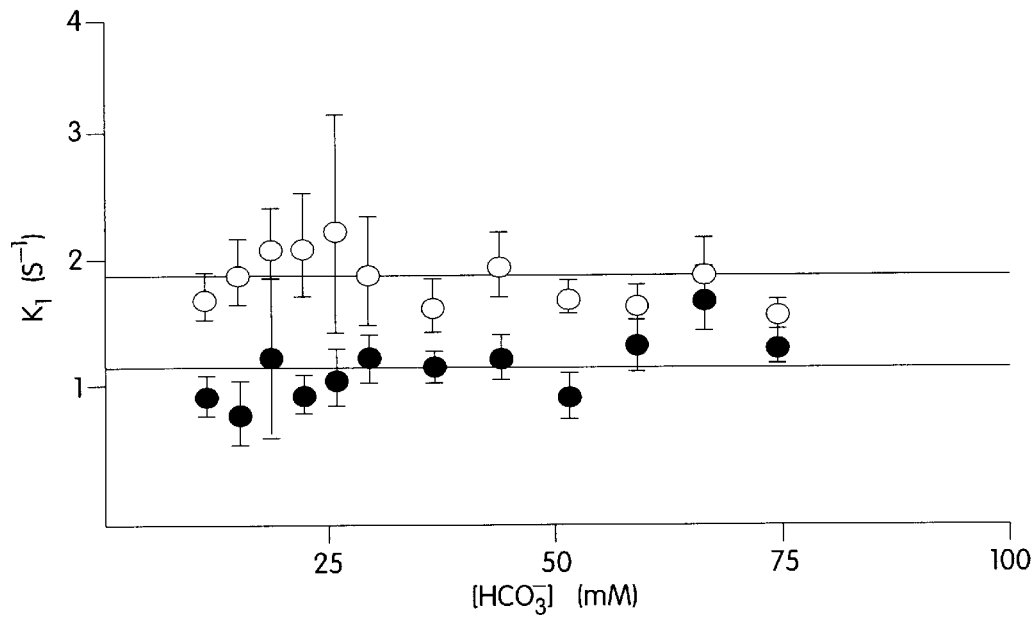
FIGS. 5A and 5B are graphs illustrating a comparison of erythrocyte anion exchange in subjects with AD and with that in individuals without AD.
Figure 5B:
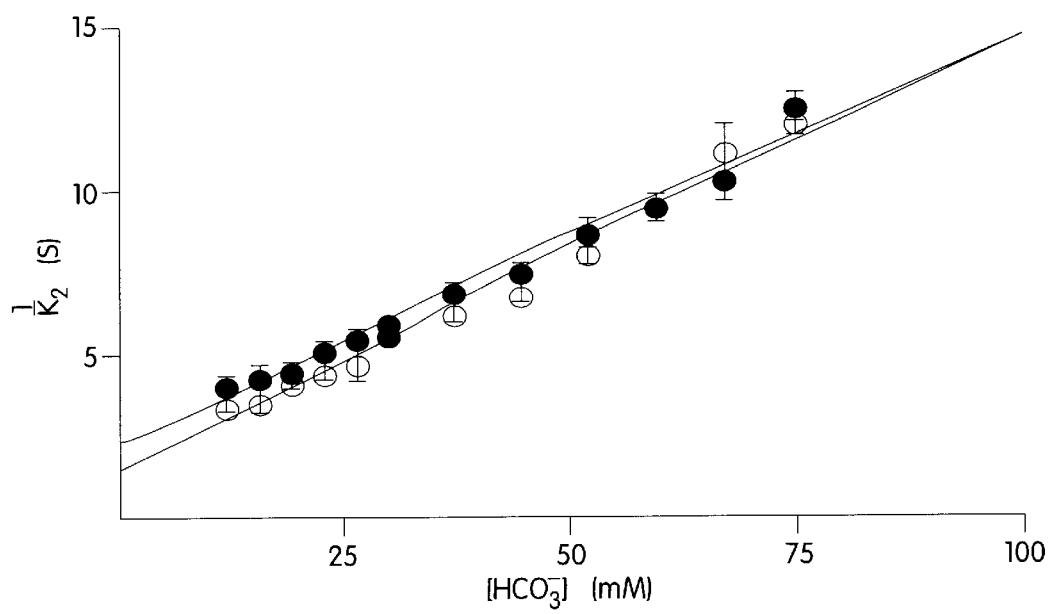

FIGS. 5A and 5B illustrate a comparison of erythrocyte anion exchange in subjects with AD with that in individuals without AD. The symbols in the figures include the following: ○=individuals with AD; ●=elderly individuals without AD. FIG. 5A is a plot of the rate constant k1 (along the vertical axis) versus [HCO₃] in mM (along the horizontal axis).

FIG. 5B is a plot of $$\frac{1}{K2}$$

(along the vertical axis) versus [HCO₃] in mM (along the horizontal axis).

As can be seen in FIG. 5A, the means of rate constant k1 differ significantly between the two populations. For individuals with AD, the mean of rate constant k1 is equal to 1.83±0.09. For individuals without AD, the mean of rate consistent k1 is equal to 1.15±0.07.

FIG. 5B, the value of $$\frac{1}{K2}$$

for those with AD is equal to 1.43±0.13 [HCO$_3$], whereas the value of $$\frac{1}{K2}$$

for healthy individuals is equal to 2.24±0.12 [HCO$_3$]. The standard error of the intercept of each line with the ordinate [when HCO$_3^-$=0] is equal to ±0.06 and the intercepts differ for the two populations. The slopes of the two plots are approximately the same.

Figure 6:
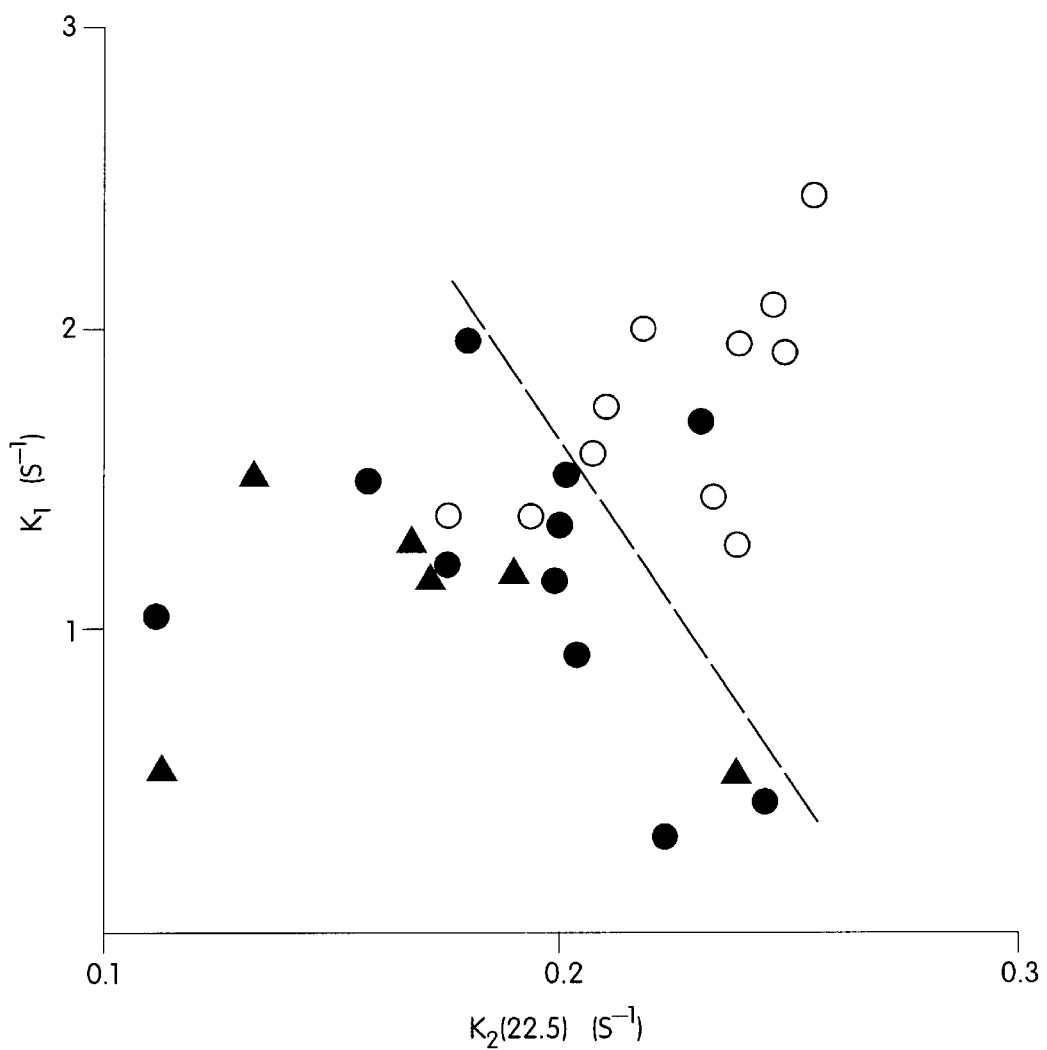
FIG. 6 is a scatter plot of one rate constant versus another rate constant for subjects with AD, elderly subjects without AD, and young adults.

FIG. 6 is a scatter plot of rate constant k1 versus rate constant k2 (22.2) for subjects with AD, elderly subjects without AD, and young adults. The symbols are as follows: ○=individuals with AD, ●=elderly individuals without AD, and ▲=young adults. For most of the subjects, as can be seen, those with AD can be distinguished from healthy individuals, regardless of age. A dashed line separates most of the subjects with AD from those without. The equation of the dashed line is equal to 0.16 k1+3.7k2(22.5)=1.

According to another preferred embodiment of the invention, measurement of the conformational changes in band 3 using a stilbene probe was conducted as follows. DBDS, 4,4'-dibenzoamido 2,2'-disulfonic stilbene, was obtained from Molecular Probes (Eugene, Oreg.). Solutions of DBDS in 150 mM NaCl, 10 mM Na$_2$HPO$_4$, pH 7.4 were prepared with [DBDS] ranging from 1 to 10 micromolar. Citrate-anticoagulated blood was washed three times in normal saline and the final pellet was resuspended to 1% hematocrit in 150 mM NaCl, 10 mM Na$_2$HPO$_4$, pH 7.4. Fluorescence measurements were performed on a Model SF.17MV Stopped-flow Spectrometer (Applied Photophysics, Leatherhead, UK). DBDS excitation was at 350 nm (9 nm bandpass) with emission measured through a 3 mm Corion cut-on filter with 50% transmission at 500 nm. Compressed air at 40 psi injected equal volumes of ghosts and DBDS mixtures into a mixing chamber; a stop syringe (0.1 ml) triggered recording. A circulating waterbath (Model 1145, VWR, Westchester, Pa.) maintained the drive syringes and mixing chamber at 4±0.1 ° C. Four hundred data points were collected over 10 s and stored in the spectrometer's workstation. Seven to ten replicate measurements were made at each [DBDS]. A change in fluorescence occurs when red cells are mixed with their suspending buffer. This baseline was subtracted from each measurement prior to curve-fitting. The mixing artifact was truncated from the data before curve-fitting.

A single exponential function, such as C(t)=De$^{(Wt)}$+Z, is fit to the obtained time course of fluorescence for each [DBDS] level, such as by an LMS method, where W is a rate constant. 1/W depends linearly on 1/[DBDS]. A straight line may be drawn for a graph of 1/W versus 1/[DBDS].

The intercept of this line with the 1/W axis can be used to classify the patient as having, or not having, AD. In one embodiment of the invention, if the intercept of the line exceeds 0.234, then the patient is classified as having AD; otherwise not.

Having thus described at least one illustrative embodiment of the invention, various alterations, modifications and improvements will readily occur to those skilled in the art. For examples, it should be appreciated that the described method for observing conformational band 3 changes as well as the equations, particular parameters particular cut-off points for patient classification, etc. are exemplary and are in no way intended to be limiting. The exact equations, parameters, cut-off points, etc. used in patient classification may be altered depending on method, conditions, data obtained, subjects, etc. Such alterations, modifications and improvements are intended to be within the spirit and scope of the invention. Accordingly, the foregoing description is by way of example only and is not intended as limiting. The invention is limited only as defined in the following claims and the equivalents thereto.

What is claimed is:

1. A method of aiding in the diagnosis of Alzheimer's Disease in a patient comprising the steps of: analyzing rate of conformational changes in a band 3 protein of the patient yielding a time course of the conformational changes; dividing the time course into first and second time periods; solving first and second single exponential functions for estimates of rate constant parameters by respectively fitting the first and second single exponential functions to the first and second time periods; and determining an increase in rate of conformational changes using at least one of the two rate constant parameter estimates.

2. The method as claimed in claim 1 further including, after the step of solving first and second single exponential functions, a step of solving a double exponential function for estimates of the two rate constant parameters.

3. The method as claimed in claim 1 wherein the step of analyzing includes obtaining a time course of fluorescence representing the conformational changes in the band 3 protein.

4. The method as claimed in claim 3 wherein the step of analyzing further includes converting the time course of fluorescence to a time course of chloride changes.

5. The method as claimed in claim 1 wherein the step of analyzing includes the steps of: preparing erythrocyte ghosts from a blood sample of the patient, wherein the ghosts contain (1) anions which are transported out of the ghosts by band 3 and (2) a fluorescent probe of the concentration of the anions; contacting the ghosts with anions which are transported into the ghosts by band 3; and measuring the fluorescence of the fluorescent probe.

6. The method as claimed in claim 5, wherein the probe is 6-methoxy-N-(3-sulfopropyl)quinolinium.

7. A method of aiding in the diagnosis of Alzheimer's Disease in a patient comprising the steps of: analyzing rate of conformational changes in a band 3 protein of the patient using a fluorescent probe of band 3 protein conformation which binds to band 3, yielding a time course of the conformational changes; solving a single exponential function for an estimate of a rate constant parameter in the single exponential function by fitting the single exponential function to the time course; and determining an increase in rate of conformational changes using the rate constant parameter estimate.

8. The method as claimed in claim 7 wherein the step of analyzing includes the steps of: preparing erythrocytes from a blood sample of the patient; contacting the erythrocytes with the fluorescent probe of band 3 protein conformation; and measuring the fluorescence of the fluorescent probe.

9. The method as claimed in claim 8, wherein the fluorescent probe is a stilbene.

10. The method as claimed in claim 9, wherein the stilbene is 4,4'-dibenzoamido 2,2'-disulfonic stilbene.

* * * * *